US007010349B2

(12) United States Patent
Conley et al.

(10) Patent No.: US 7,010,349 B2
(45) Date of Patent: *Mar. 7, 2006

(54) SYSTEM AND METHOD FOR DETECTING AND DISPLAYING PARAMETER INTERACTIONS

(75) Inventors: Vickie L. Conley, Woodbury, MN (US); Allan T. Koshiol, Lino Lakes, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/731,282

(22) Filed: Dec. 9, 2003

(65) Prior Publication Data

US 2004/0116982 A1 Jun. 17, 2004

Related U.S. Application Data

(63) Continuation of application No. 09/921,349, filed on Aug. 2, 2001, now Pat. No. 6,690,972, which is a continuation of application No. 09/378,405, filed on Aug. 20, 1999, now Pat. No. 6,289,248.

(51) Int. Cl.
*A61N 1/36* (2006.01)
(52) U.S. Cl. .............................. 607/31; 607/59; 607/63
(58) Field of Classification Search ........ 600/522–523; 128/897–898; 607/5, 30–32, 59, 63
See application file for complete search history.

(56) References Cited

U.S. PATENT DOCUMENTS

| 4,006,737 | A | 2/1977 | Cherry | 128/2.06 G |
|---|---|---|---|---|
| 4,090,505 | A | 5/1978 | Mortara | 128/2.06 G |
| 4,166,470 | A | 9/1979 | Neumann | 128/419 PG |
| 4,172,459 | A | 10/1979 | Hepp | 128/697 |
| 4,187,854 | A | 2/1980 | Hepp et al. | 128/419 PG |
| 4,197,850 | A | 4/1980 | Schulman et al. | 128/419 PG |
| 4,208,008 | A | 6/1980 | Smith | 371/15 |
| 4,232,679 | A | 11/1980 | Schulman | 128/419 PG |
| 4,236,524 | A | 12/1980 | Powell et al. | 128/419 PT |
| 4,316,249 | A | 2/1982 | Gallant et al. | 364/417 |
| 4,323,074 | A | 4/1982 | Nelms | 128/419 PG |
| 4,336,810 | A | 6/1982 | Anderson et al. | 128/702 |
| 4,407,288 | A | 10/1983 | Langer et al. | 128/419 PG |
| 4,432,360 | A | 2/1984 | Mumford et al. | 128/419 PG |

(Continued)

FOREIGN PATENT DOCUMENTS

EP 0565084 10/1993

(Continued)

*Primary Examiner*—Robert E. Pezzuto
*Assistant Examiner*—Kristen Mullen
(74) *Attorney, Agent, or Firm*—Schwegman, Lundberg, Woessner & Kluth, P.A.

(57) ABSTRACT

A system and method of detecting and displaying parameter interactions. A medical device system has a medical device and a programming interface, wherein the medical device includes a plurality of features which can be programmed via the programming interface. A plurality of icons is defined, wherein the plurality of icons includes a first icon, a second icon and a third icon, wherein the first icon indicates correctness, wherein the second icon warns of a parameter interaction and wherein the third icon warns of impermissible parameter settings. Parameter interactions between feature parameters are identified and each of the parameter interactions is associated with one of the plurality of icons. A parameter value is accepted and examined to determine if it causes a parameter interaction. If the parameter value causes a parameter interaction, the icon associated with the parameter interaction is displayed.

25 Claims, 9 Drawing Sheets

U.S. PATENT DOCUMENTS

| | | | |
|---|---|---|---|
| 4,509,530 A | 4/1985 | Curtis et al. ............... 128/710 |
| 4,529,401 A | 7/1985 | Leslie et al. ............... 604/131 |
| 4,549,552 A | 10/1985 | Groch et al. ............... 128/700 |
| 4,680,708 A | 7/1987 | Ambos et al. .............. 364/417 |
| 4,726,380 A | 2/1988 | Vollmann et al. ...... 128/419 PG |
| 4,809,697 A | 3/1989 | Causey, III et al. ... 128/419 PT |
| 4,825,869 A | 5/1989 | Sasmor et al. ......... 128/419 PT |
| 4,947,857 A | 8/1990 | Albert et al. ............... 128/696 |
| 4,958,632 A | 9/1990 | Duggan ................. 128/419 PG |
| 4,974,598 A | 12/1990 | John ......................... 128/696 |
| 4,989,610 A | 2/1991 | Patton et al. ............... 128/695 |
| 5,000,189 A | 3/1991 | Throne et al. .............. 128/702 |
| 5,012,814 A | 5/1991 | Mills et al. ................. 128/691 |
| 5,027,824 A | 7/1991 | Dougherty et al. ......... 128/702 |
| 5,046,504 A | 9/1991 | Albert et al. ............... 128/696 |
| 5,047,930 A | 9/1991 | Martens et al. ........ 364/413.04 |
| 5,050,612 A | 9/1991 | Matsumura ................. 128/670 |
| 5,052,395 A | 10/1991 | Burton et al. .......... 128/661.09 |
| 5,107,850 A | 4/1992 | Olive ......................... 128/705 |
| 5,113,869 A | 5/1992 | Nappholz et al. ........... 128/696 |
| 5,184,614 A | 2/1993 | Collins et al. ........ 128/419 PG |
| 5,193,550 A | 3/1993 | Duffin ........................ 129/697 |
| 5,215,083 A | 6/1993 | Drane et al. ............ 128/419 D |
| 5,224,475 A | 7/1993 | Berg et al. .............. 128/419 D |
| 5,273,049 A | 12/1993 | Steinhaus et al. ........... 128/696 |
| 5,292,341 A | 3/1994 | Snell ........................... 607/30 |
| 5,299,118 A | 3/1994 | Martens et al. ........ 364/413.05 |
| 5,309,919 A | 5/1994 | Snell et al. ................. 128/697 |
| 5,311,873 A | 5/1994 | Savard et al. ............... 128/696 |
| 5,311,874 A | 5/1994 | Baumann et al. ........... 128/705 |
| 5,312,448 A | 5/1994 | Hognelid et al. ............. 607/13 |
| 5,315,512 A | 5/1994 | Roth ..................... 364/413.25 |
| 5,341,811 A | 8/1994 | Cano .......................... 128/696 |
| 5,342,402 A | 8/1994 | Olson et al. ................... 607/5 |
| 5,344,430 A | 9/1994 | Berg et al. ..................... 607/8 |
| 5,360,437 A | 11/1994 | Thompson ................... 607/30 |
| 5,379,776 A | 1/1995 | Murphy et al. ............. 128/705 |
| 5,400,795 A | 3/1995 | Murphy et al. ............. 128/702 |
| 5,404,877 A | 4/1995 | Nolan et al. ................ 128/671 |
| 5,411,528 A | 5/1995 | Miller et al. ................... 607/5 |
| 5,421,830 A | 6/1995 | Epstein et al. ................ 607/30 |
| 5,423,871 A | 6/1995 | Hoegnelid et al. ............ 607/28 |
| 5,433,198 A | 7/1995 | Desai ......................... 128/642 |
| 5,458,623 A | 10/1995 | Lu et al. ....................... 607/28 |
| 5,464,433 A | 11/1995 | White et al. ................... 607/5 |
| 5,480,422 A | 1/1996 | Ben-Haim .................. 607/122 |
| 5,487,754 A | 1/1996 | Snell et al. ................... 607/27 |
| 5,487,755 A | 1/1996 | Snell et al. ................... 607/27 |
| 5,496,351 A | 3/1996 | Plicchi et al. ................. 607/17 |
| 5,507,786 A | 4/1996 | Morgan et al. ............... 607/27 |
| 5,513,645 A | 5/1996 | Jacobson et al. ........... 128/710 |
| 5,523,942 A | 6/1996 | Tyler et al. ................. 364/401 |
| 5,535,753 A | 7/1996 | Petrucelli et al. ........... 128/672 |
| 5,549,646 A | 8/1996 | Katz et al. ..................... 607/8 |
| 5,549,654 A | 8/1996 | Powell ......................... 607/32 |
| 5,555,888 A | 9/1996 | Brewer et al. .............. 128/702 |
| 5,578,063 A | 11/1996 | Bocek et al. ................... 607/5 |
| 5,584,298 A | 12/1996 | Kabal ......................... 128/672 |
| 5,603,331 A | 2/1997 | Heemels et al. ............ 128/696 |
| 5,607,460 A | 3/1997 | Kroll et al. ................... 607/30 |
| 5,609,612 A | 3/1997 | Plicchi et al. ................. 607/17 |
| 5,613,495 A | 3/1997 | Mills et al. ................. 128/696 |
| 5,620,471 A | 4/1997 | Duncan ........................ 607/14 |
| 5,620,472 A | 4/1997 | Rahbari ........................ 607/27 |
| 5,620,474 A | 4/1997 | Koopman .................... 607/29 |
| 5,626,620 A | 5/1997 | Kieval et al. ................... 607/9 |
| 5,626,623 A | 5/1997 | Kieval et al. ................. 607/23 |
| 5,628,321 A | 5/1997 | Scheib et al. ........... 128/661.08 |
| 5,643,255 A | 7/1997 | Organ ......................... 606/41 |
| 5,647,369 A | 7/1997 | Petrucelli et al. ........... 128/672 |
| 5,674,249 A | 10/1997 | de Coriolis et al. ............. 607/5 |
| 5,683,431 A | 11/1997 | Wang .......................... 607/28 |
| 5,687,737 A | 11/1997 | Branham et al. ........... 128/710 |
| 5,693,075 A | 12/1997 | Plicchi et al. ................. 607/17 |
| 5,697,959 A | 12/1997 | Poore .......................... 607/32 |
| 5,713,366 A | 2/1998 | Armstrong et al. |
| 5,713,937 A | 2/1998 | Nappholz et al. ............. 607/30 |
| 5,716,382 A | 2/1998 | Snell ........................... 607/30 |
| 5,716,383 A | 2/1998 | Kieval et al. ................... 607/9 |
| 5,716,384 A | 2/1998 | Snell ........................... 607/30 |
| 5,722,999 A | 3/1998 | Snell ........................... 607/32 |
| 5,724,985 A | 3/1998 | Snell et al. ................. 128/697 |
| 5,725,559 A | 3/1998 | Alt et al. ........................ 607/5 |
| 5,743,268 A | 4/1998 | Kabal ......................... 128/691 |
| 5,749,900 A | 5/1998 | Schroeppel et al. ............ 607/4 |
| 5,749,906 A | 5/1998 | Kieval et al. ................... 607/9 |
| 5,749,907 A | 5/1998 | Mann .......................... 607/27 |
| 5,755,736 A | 5/1998 | Gillberg et al. ................ 607/4 |
| 5,755,742 A | 5/1998 | Schuelke et al. ............. 607/27 |
| 5,759,199 A | 6/1998 | Snell et al. ................... 607/60 |
| 5,772,604 A | 6/1998 | Langberg et al. ........... 600/518 |
| 5,785,660 A | 7/1998 | van Lake et al. ........... 600/523 |
| 5,788,640 A | 8/1998 | Peters ........................ 600/483 |
| 5,792,203 A | 8/1998 | Schroeppel .................. 607/30 |
| 5,792,204 A | 8/1998 | Snell ........................... 607/32 |
| 5,803,084 A | 9/1998 | Olson ......................... 128/699 |
| 5,810,740 A | 9/1998 | Paisner ....................... 600/515 |
| 5,814,088 A | 9/1998 | Paul et al. .................... 607/28 |
| 5,817,137 A | 10/1998 | Kaemmerer ................. 607/59 |
| 5,833,623 A | 11/1998 | Mann et al. ................. 600/523 |
| 5,836,989 A | 11/1998 | Shelton ........................ 607/27 |
| 5,839,989 A | 11/1998 | Saito et al. ................. 477/143 |
| 5,843,138 A | 12/1998 | Evers et al. .................. 607/30 |
| 5,876,353 A | 3/1999 | Riff ............................ 600/547 |
| 5,891,043 A | 4/1999 | Ericksen et al. ............ 600/508 |
| 5,891,178 A | 4/1999 | Mann et al. ................... 607/27 |
| 5,891,179 A | 4/1999 | Er et al. ....................... 607/27 |
| 5,897,577 A | 4/1999 | Cinbis et al. ................. 607/28 |
| 5,908,392 A | 6/1999 | Wilson et al. .............. 600/509 |
| 5,924,989 A | 7/1999 | Polz ........................... 600/443 |
| 5,951,484 A | 9/1999 | Hoium et al. ............... 600/515 |
| 5,954,664 A | 9/1999 | Seegobin .................... 600/515 |
| 5,957,856 A | 9/1999 | Weil et al. .................. 600/518 |
| 5,957,861 A | 9/1999 | Combs et al. ............... 600/547 |
| 5,961,467 A | 10/1999 | Shimazu et al. ............ 600/485 |
| 5,974,341 A | 10/1999 | Er et al. ....................... 607/31 |
| 5,978,707 A | 11/1999 | Krig et al. .................... 607/14 |
| 6,004,020 A | 12/1999 | Bartur .................... 364/479.06 |
| 6,004,276 A | 12/1999 | Wright et al. ............... 600/508 |
| 6,007,493 A | 12/1999 | Ericksen et al. ............ 600/508 |
| 6,014,581 A | 1/2000 | Whayne et al. ............. 600/523 |
| 6,016,442 A | 1/2000 | Hsu et al. .................... 600/518 |
| 6,016,447 A | 1/2000 | Juran et al. ................... 607/27 |
| 6,016,448 A | 1/2000 | Busacker et al. ............. 607/29 |
| 6,017,307 A | 1/2000 | Raines ........................ 600/300 |
| 6,035,233 A | 3/2000 | Schroeppel et al. ........ 600/515 |
| 6,045,513 A | 4/2000 | Stone et al. ................. 600/508 |
| 6,073,049 A | 6/2000 | Alt et al. ...................... 607/31 |
| 6,088,618 A | 7/2000 | Kerver ........................ 607/30 |
| 6,091,990 A | 7/2000 | Hsu et al. ....................... 607/5 |
| 6,101,415 A | 8/2000 | Er et al. ....................... 607/27 |
| 6,101,416 A | 8/2000 | Sloman ........................ 607/28 |
| 6,151,524 A | 11/2000 | Krig et al. .................... 607/14 |
| 6,240,317 B1 | 5/2001 | Villaseca et al. ............. 607/60 |
| 6,253,102 B1 | 6/2001 | Hsu et al. .................... 600/515 |
| 6,289,244 B1 | 9/2001 | Conley et al. ................ 607/27 |
| 6,289,248 B1 | 9/2001 | Conley et al. ................ 607/59 |
| 6,301,503 B1 | 10/2001 | Hsu et al. ..................... 607/30 |
| 6,308,095 B1 | 10/2001 | Hsu et al. .................... 600/518 |

| | | | |
|---|---|---|---|
| 6,317,632 B1 | 11/2001 | Krig et al. | 607/14 |
| 6,321,117 B1 | 11/2001 | Koshiol et al. | 607/59 |
| 6,400,981 B1 | 6/2002 | Govari | 600/509 |
| 6,415,175 B1 | 7/2002 | Conley et al. | 600/523 |
| 6,445,952 B1 | 9/2002 | Manrodt et al. | 607/28 |
| 6,454,726 B1 | 9/2002 | Catt et al. | 600/551 |
| 6,493,579 B1 | 12/2002 | Gilkerson et al. | 607/5 |
| 6,690,972 B1 * | 2/2004 | Conley et al. | 607/31 |
| 2004/0111131 A1 | 6/2004 | Hu et al. | 607/60 |

FOREIGN PATENT DOCUMENTS

WO    WO-99/27992    6/1999

* cited by examiner

SYSTEM AND METHOD FOR DETECTING AND DISPLAYING PARAMETER INTERACTIONS

CROSS-REFERENCE TO RELATED APPLICATION(S)

This application is a continuation of U.S. patent application Ser. No. 09/921,349 filed on Aug. 2, 2001, now issued as U.S. Pat. No. 6,690,972, which is a continuation of U.S. patent application Ser. No. 09/378,405, filed on Aug. 20, 1999, now issued as U.S. Pat. No. 6,289,248, the specifications of which are incorporated herein by reference.

FIELD OF THE INVENTION

The present invention is related to medical device programming, and more particularly to a system and method for detecting and displaying parameter interactions arising during the programming of a medical device.

BACKGROUND INFORMATION

As medical device feature sets become richer and more complex, medical devices are getting increasingly complicated to program. This is especially the case in situations where modification of one feature ripples through and interacts with other selected features.

For devices such as implantable cardioverter defibrillators it can be very difficult for physicians to deal with non-compatibilities with programming. Such devices may have many features to program and, when physicians go in to program, there may be some inconsistencies that are not allowed by logic or by concerns for safety of the patient. In the past, these inconsistencies were displayed as error messages and the physician often had to wade through a series of screens to determine the nature of the inconsistency and how to resolve it.

In addition, physicians were frustrated by error messages which noted an interaction but did not tell them what to do to resolve the problem. They were often reduced to trial and error programming which might create a second parameter interaction while resolving the first.

What is needed is a more intuitive way for the physician to resolve parameter interactions.

SUMMARY OF THE INVENTION

According to one aspect of the present invention, a system and method of detecting and displaying parameter interactions is described for use in a medical device system having a medical device and a programming interface, wherein the medical device includes a plurality of features which can be programmed via the programming interface. A plurality of icons is defined, wherein the plurality of icons includes a first icon, a second icon and a third icon, wherein the first icon indicates correctness, wherein the second icon warns of a parameter interaction and wherein the third icon warns of impermissible parameter settings. Parameter interactions between feature parameters are identified and each of the parameter interactions is associated with one of the plurality of icons. A parameter value is accepted and examined to determine if it causes a parameter interaction. If the parameter value causes a parameter interaction, the icon associated with the parameter interaction is displayed.

According to another aspect of the present invention, a system and method of detecting and displaying parameter interactions is described for use in a medical device system having a medical device and a programming interface, wherein the medical device includes a plurality of features which can be programmed via the programming interface. A plurality of messages is defined, wherein the plurality of messages includes a first type of message, a second type of message and a third type of message, wherein the first type of message indicates correctness, wherein the second type of message warns of a parameter interaction and wherein the third type of message warns of impermissible parameter settings. Parameter interactions between feature parameters are identified and each of the parameter interactions is associated with one of the message types. A parameter value is accepted and examined to determine if it causes a parameter interaction. If the parameter value causes a parameter interaction, the message of the message type associated with the parameter interaction is displayed.

According to yet another aspect of the present invention, a system and method of detecting and correcting parameter interactions is described for use in a medical device system having a medical device and a programming interface, wherein the medical device includes a plurality of features which can be programmed via the programming interface. Parameter interactions between feature parameters are identified. A parameter value is accepted and examined to determine if it causes a parameter interaction. If the parameter value causes a parameter interaction, a message representative of the parameter interaction is displayed. The message includes a description of the parameter interaction and one or more parameters. One or more of the displayed parameters is modified and the modified parameter value is examined to determine if it causes a parameter interaction.

In yet another aspect of the present invention, a medical device system is described. The medical device system includes a medical device and a programming interface. The medical device includes a plurality of features which can be programmed via the programming interface. The programming interface includes a display for displaying a plurality of icons and rules identifying parameter interactions between feature parameters and rules associating each of the parameter interactions with one of the plurality of icons. The programming interface accepts a parameter value, examines the parameter value to determine if it causes a parameter interaction and, if the parameter value causes a parameter interaction, displays the icon associated with the parameter interaction.

BRIEF DESCRIPTION OF THE DRAWINGS

In the drawings, where like numerals refer to like components throughout the several views.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural changes may be made without departing from the scope of the present invention.

Some portions of the detailed descriptions which follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. It should be borne in mind, however, that all of these and similar terms are to be associated with the appropriate physical quantities and are merely convenient labels applied to these quantities. Unless specifically stated otherwise as apparent from the following discussions, it is appreciated that throughout the present invention, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Figure 1:
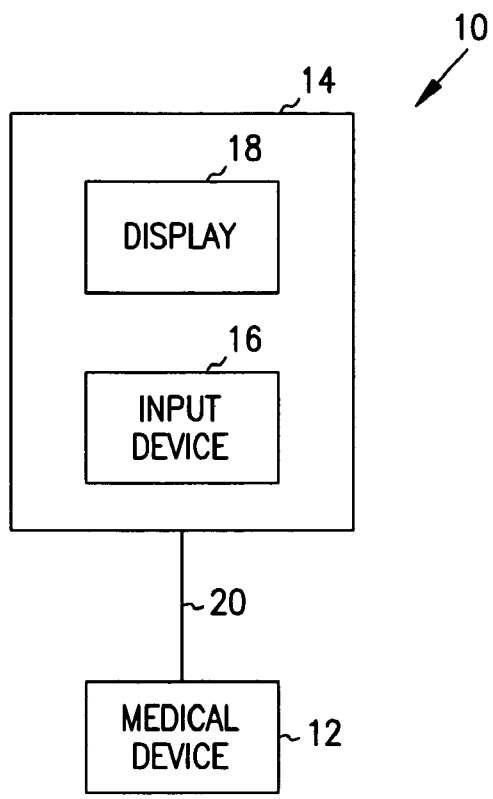
FIG. 1 illustrates a medical device system according to the present invention.

FIG. 1 illustrates a medical device system 10 with the inventive parameter interaction detection and display feature. Medical device system 10 includes a medical device 12 and a programmer 14. Programmer 14 includes an input device 16 and a display 18 and is connected to medical device 12 via communications link 20. Communications link 20 may embody any form of communications protocol, including wired, wireless, optical and other forms of communication protocols. Input device 16, display 18 and the underlying hardware and software make up the programming interface.

Features of medical device 12 are displayed on display 18 and may be modified through the use of input device 16. Parameter interactions between these features are also displayed on display 18 in the manner described below.

Figure 2:
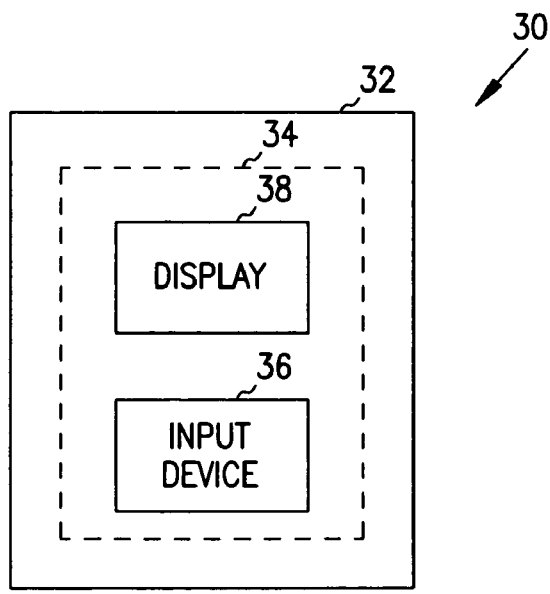
FIG. 2 illustrates an alternate embodiment of a medical device system according to the present invention.

FIG. 2 illustrates a medical device system 30 with the inventive parameter interaction detection and display feature. Medical device system 30 includes a medical device 32 with a built-in programming interface 34. Programming interface 34 includes an input device 36 and a display 38. Features of medical device 32 are displayed on display 38 and may be modified through the use of input device 36. Parameter interactions between these features are also displayed on display 38 in the manner described below.

Figure 3:
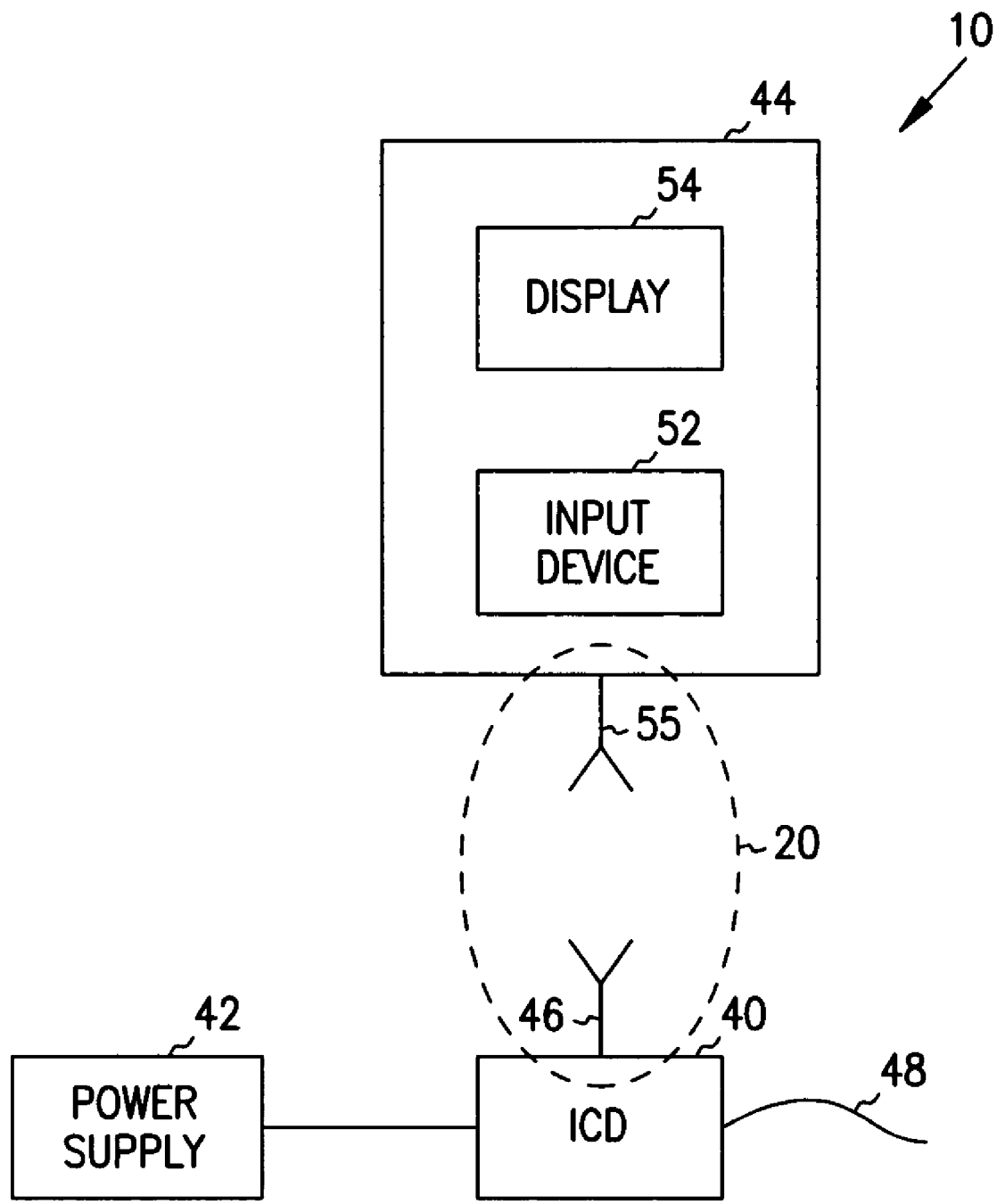
FIG. 3 illustrates one embodiment of an implantable cardioverter defibrillator medical device system according to the present invention.

In one embodiment, medical device system 10 is an implantable shock therapy system. Such a medical device system 10 is shown in FIG. 3. In FIG. 3, medical device system 10 includes a defibrillator 40, a power supply 42 and a programmer 44. Power supply 42 is connected to defibrillator 40 and supplies power to defibrillator 40. Defibrillator 40 is connected to programmer 44 via communications link 20.

In one such embodiment, defibrillator 40 includes a telemetry system 46 for communicating with programmer 44. In addition, defibrillator 40 supplies the requisite therapy to the heart via leads 48.

Programmer 44 includes an input device 52 such as a keyboard or mouse, a display 54 and telemetry system 55. Features selected or programmed by physicians into programmer 44 are communicated through telemetry to defibrillator 40, where they control shock and pacing therapy applied to the patient's heart.

In one embodiment, systems 10 and 20 include interactive programming feedback. Interactive programming feedback is a feature that is designed to assist the user in programming the medical device appropriately. In one such embodiment, a set of rules govern the universe of possibilities that the various parameters may be programmed to. The rules ensure that incompatibilities among features are caught and prevented and that programming conflicts cannot exist. In one such embodiment, if a user programs a parameter in such a way that an incompatibility exists, programmer 14 or 44, or programming interface 34, provides a visual indication on the respective display to inform the user of the situation, and provides on-screen guidance as to how to correct the situation. In addition, when the user attempts to correct the programming error, systems 10 and 20 provide immediate feedback as to the success of the correction.

Figure 4:
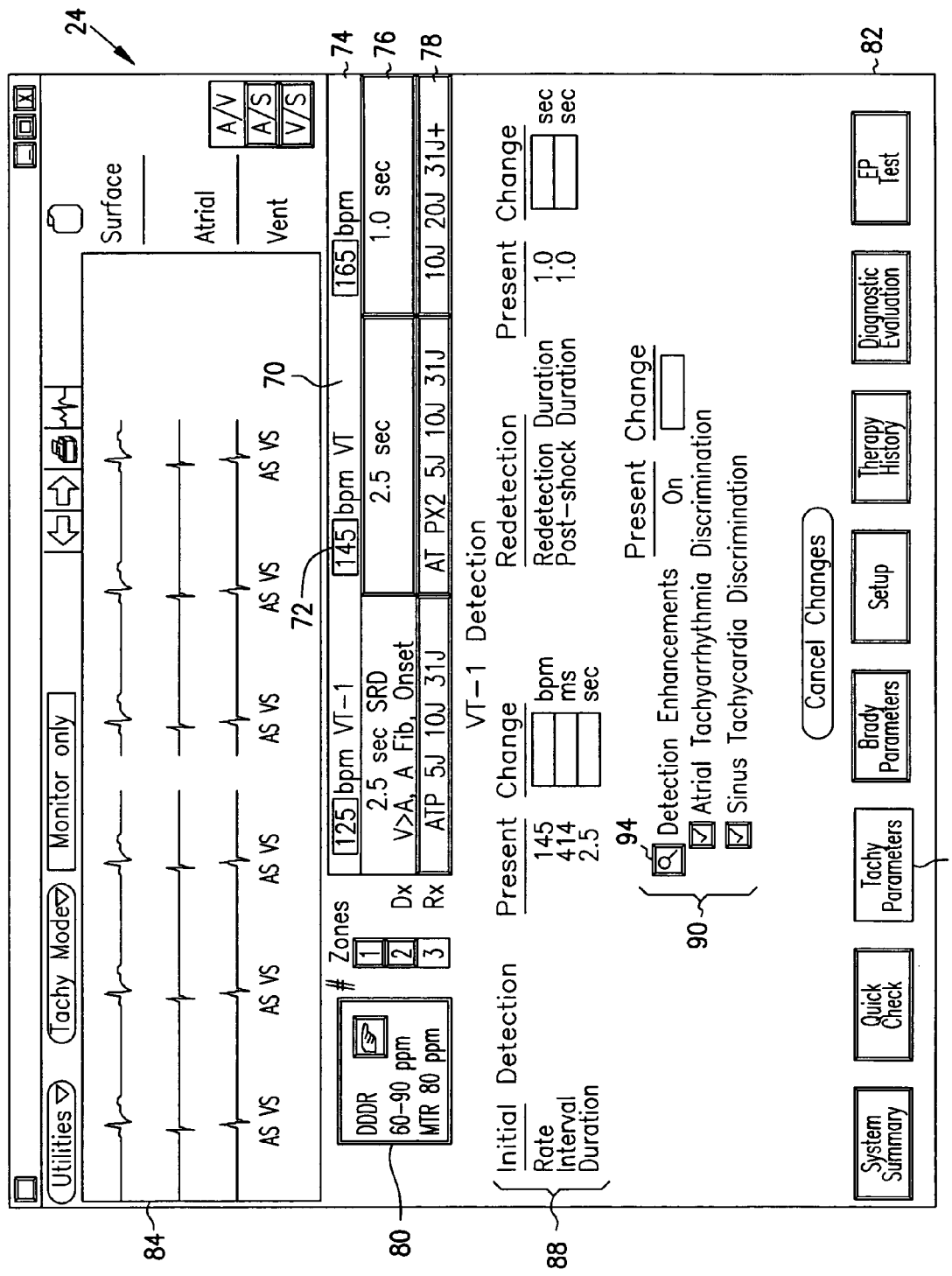
FIG. 4 illustrates a display for use in a implantable cardioverter defibrillator.

A display which could be used to control systems 10 and 20 is shown in FIG. 4. The display in FIG. 4 is geared toward the defibrillator system shown in FIG. 3 but can be generalized to control of any medical device 12 or 32.

Representative three zone configurations are shown in FIG. 4. In the embodiment shown in FIG. 4, system 10 includes up to three tachyarrhythmia zones (labeled as VT-1, VT, and VF). In one such embodiment, such as is shown in FIG. 4, each zone is identified on display 24 with its label 70 and its rate threshold 72. In the embodiment shown in FIG. 4, label 70 and its associated rate threshold 72 are displayed within a zone rate bar 74. In addition, a detection summary for each zone is displayed within detection button 76 for that zone and a therapy summary for each zone is displayed within therapy button 78 for that zone.

Figure 5:
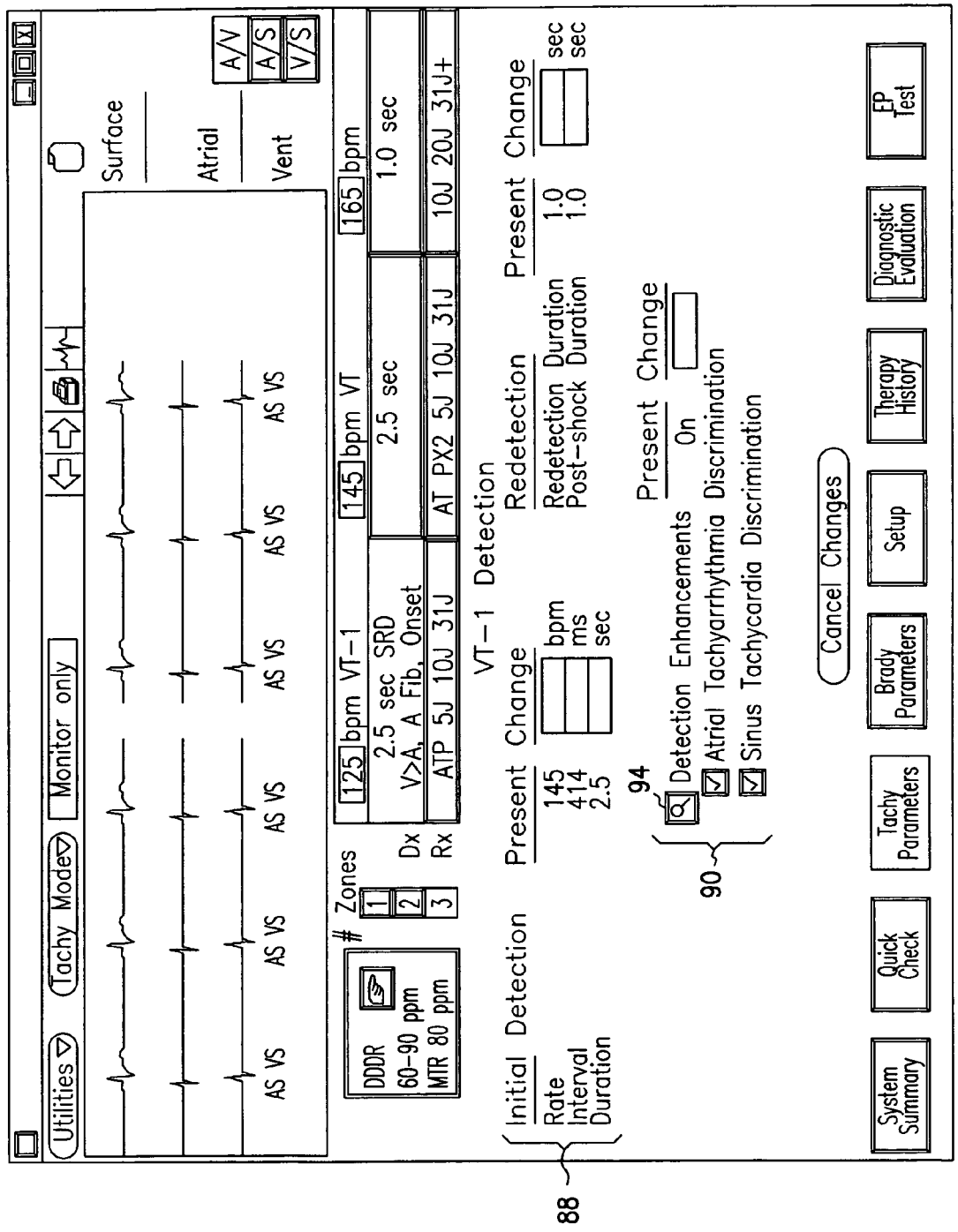
FIG. 5 illustrates another display for use in a implantable cardioverter defibrillator.

In one embodiment, the user accesses the detection parameters for a zone by selecting the respective detection button 76 and accesses the therapy parameters for a zone by selecting the respective therapy button 78. If a zone's detection button 76 has been selected, the initial and redetection parameters 88 are displayed for that zone. For example, FIG. 4 illustrates the initial and redetection parameters associated with the VT-1 zone, while FIG. 5 illustrates the initial and redetection parameters associated with the VT zone. Detection enhancement rhythm discrimination categories 90 (see FIGS. 4 and 5) are displayed as well for those zones in which enhancements are available. In one embodiment, the user selects rate threshold value 72 in order to change the rate threshold for that zone.

In the embodiment shown in FIGS. 4 and 5, the number of zones tachyarrhythmia zones can be modified by selecting one of the number buttons beneath the "# Zones" label.

In one embodiment, if parameter settings have changed but have not yet been programmed into the pulse generator, hatch marks (////) will appear in the summary area. When the values are programmed, the hatch marks disappear.

In one embodiment, a subset of zone configuration information is displayed when the system summary and quick check screens are visible, which allows a shortcut to the detection and/or therapy parameters screens. (Only presently programmed values are displayed; it does not display changed data that has not yet been programmed into the device nor hatch marks.) In one embodiment, the user selects a shortcut icon to navigate to the Tachy Parameters screen, which displays detailed information. If a shortcut icon appears dim, it indicates that a change to the number of zones has not been programmed; thus a shortcut is not available to the parameter screens.

A brady therapy summary 80 is also visible in FIGS. 4 and 5. This area displays the normal and post-shock bradycardia modes and rates. Additional bradycardia parameter settings may be viewed and changed by selecting the brady summary button when a shortcut icon is visible, or the Brady Parameters tool. Depending on which toolbox screen is visible, this summary button may show just the rate/zone bar or may include additional information as is shown in FIGS. 4 and 5.

Toolbox 82 displays various features depending on the chosen toolbox button. The features allow interaction with the pulse generator as well as a review of data in pulse generator memory. Only one tool may be selected at a time. (In one embodiment, the System Summary tool is selected when the application is initially accessed. However, if an episode is in progress at initial interrogation, the EP Test screen will be displayed.)

In the embodiment shown in FIGS. 4 and 5, windows contain information relevant to a particular function. They may include names of pulse generator parameters and functions, value boxes to accommodate value changes, buttons to open additional windows, and buttons to cancel changes or close the window. To remove the window from the display, select the button that initiates activity or select the Close or Cancel button.

Message windows are used to provide feedback during communication sessions. Some require action as indicated in the window before continuing the session, while others simply relay information without requiring further action or show status of an activity. Many message windows have a Cancel or Close button; select the desired button to cancel the action being performed as explained in the message and/or close the window.

In the embodiment shown in FIGS. 4 and 5, ECG display 84 is always visible. ECG display 84 shows real-time surface ECG traces, as well as real-time electrograms (EGMs) and event markers, which are useful in ascertaining system performance. In one such embodiment, a 20-second snapshot of the ECG trace, electrograms, and markers can be printed automatically; when the cursor is positioned over the ECG display the cursor changes to a camera icon; click the left trackball key to "capture" the trace. The printed trace shows 10 seconds before and 10 seconds after the moment of command.

In one embodiment, annotated event markers identify certain intrinsic cardiac and device-related events, and provide information such as sensed/paced events, decision of detection criteria, and therapy delivery. The markers are displayed on ECG display 84.

In one embodiment, real-time electrograms can be transmitted from the pace/sense or shocking electrodes to evaluate lead system integrity such as lead fractures, insulation breaks, or dislodgments.

The number of zones, the zones' rate thresholds, and values for detection, redetection, and detection enhancement parameters can be programmed from the Zone Configuration display in FIGS. 4 and 5 in the following manner.

First, select Tachy Parameters button 86 from toolbox 82 to display the zone configuration area and the selected zone's parameters. Next, change the number of zones by selecting the desired number (1, 2, or 3) from the #Zones column. The zone configuration will display the selected number of zones with hatch marks overlaying the new zones, which have not been programmed into the device yet. Third, change the rate threshold using either select box 72 from zone/rate bar 74 or via the zone's detection button 76.

Next, change any of the desired initial or redetection parameters. In one embodiment, hatch marks overlay the zone's detection button 76 until the changed parameters have been programmed into the pulse generator. Note: As parameter values are changed, the information icon and/or stop sign icon may appear at the top of the main application screen to inform of potential parameter interactions. Modify parameters as required to get around these objections. Detection and display of parameter interaction will be further discussed below.

Magnifying-glass icon 94 can be used ro display feature parameters. In addition, a number of details are shown in FIGS. 4 and 5. For instance, detection enhancement details for VT-1 zone are shown in FIG. 4 while detection enhancement details for VT zone are shown in FIG. 5.

Detection enhancement parameters can be more easily programmed by identifying the type of rhythm discrimination desired and associating the clinical rhythms with particular detection enhancements. In one embodiment, the types of clinical rhythms include: atrial tachyarrhythmia, sinus tachycardia, and polymorphic VT. See "System And Method For Detection Enhancement Programming," filed herewith, for more information on detection enhancement programming through the use of clinical rhythms.

Figure 6:
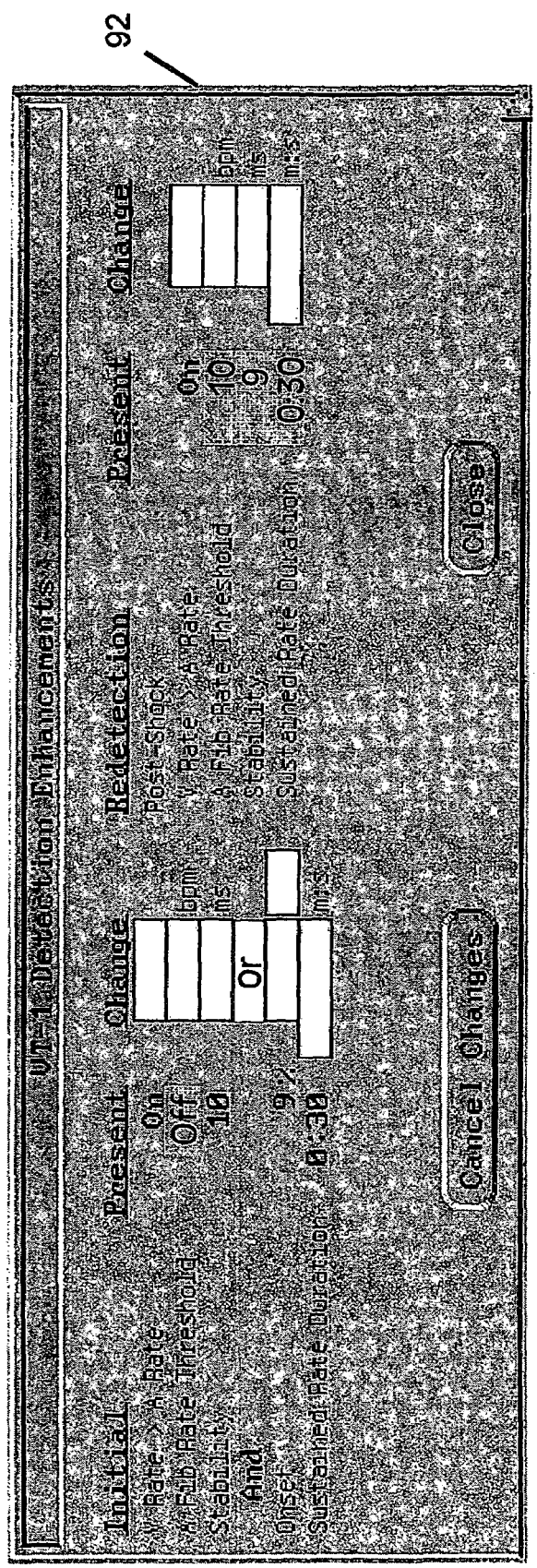
FIG. 6 illustrates a display for modifying detection enhancement parameters in a implantable cardioverter defibrillator.
Figure 7:
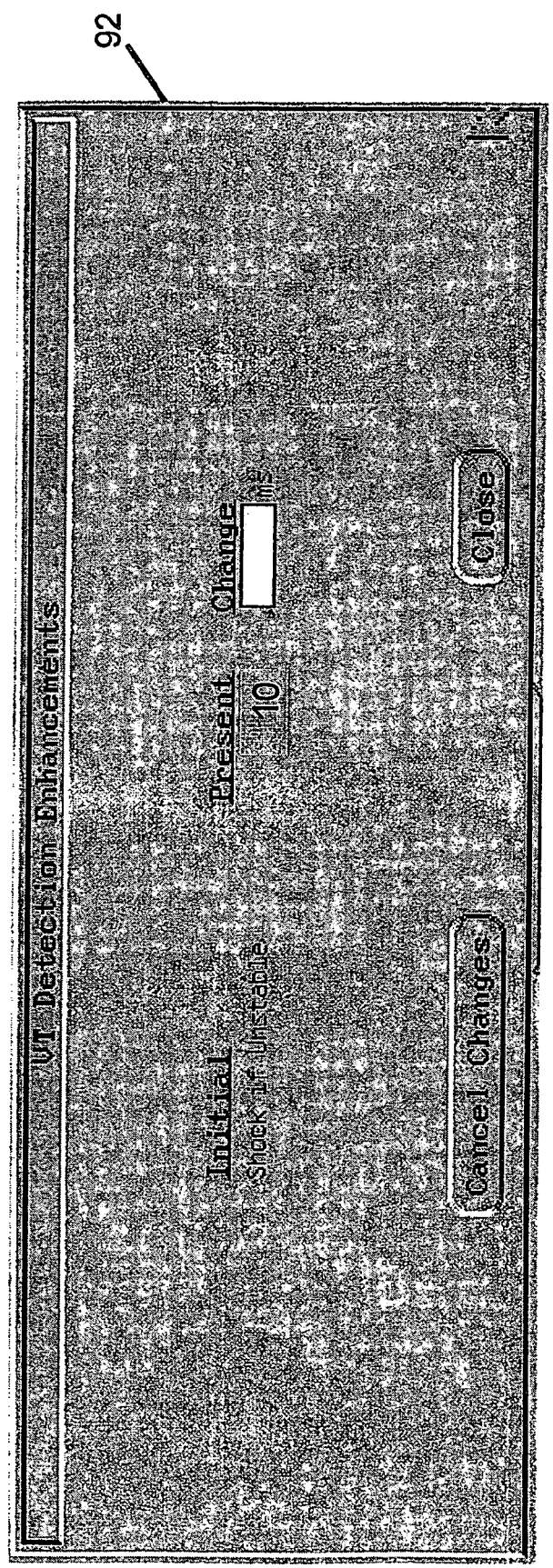
FIG. 7 illustrates another display for modifying detection enhancement parameters in a implantable cardioverter defibrillator.

When a rhythm discrimination is selected, preselected values are displayed for the parameters that are suitable for discriminating that rhythm. From a zone's detection screen (window 92 in FIGS. 6 and 7), detection parameters can be turned On by selecting the Detection Enhancements On or Off value box, or by selecting the individual rhythm types. Window 92 is closed when the parameters values are as desired.

As noted above, systems 10 and 20 provide almost immediate feedback of parameters interactions and how to correct them. In one embodiment, once the user has attempted to program an incompatible setting, systems 10 and 20 display a written message that describes the problem to the user. The written description of the programming conflict describes why the programming change is not allowed, and what specific parameters need to be changed in order to correct the problem. If more than one option is available to correct the incompatibility, all choices are displayed.

In one embodiment, systems 10 and 20 list each of the parameters in question that may need to be adjusted, and a status icon for each. In one such embodiment, the visual display of the interactive feedback includes the use of icons to signify the status of the programming change. If a red stop sign is displayed, the programming change violates a rule of programming, and thus needs to be corrected before the system will allow programming of the medical device. If a yellow warning sign is displayed, the programming change is allowable, but caution should be used as to the limitations that may occur when the device is programmed as such. On seeing a red stop sign or a yellow warning sign, the user has the opportunity to change one or more programming parameter values. If the user does so and a green check mark or exclamation point is displayed, the programming change has corrected the issue, and thus no further programming is necessary.

Figure 8:
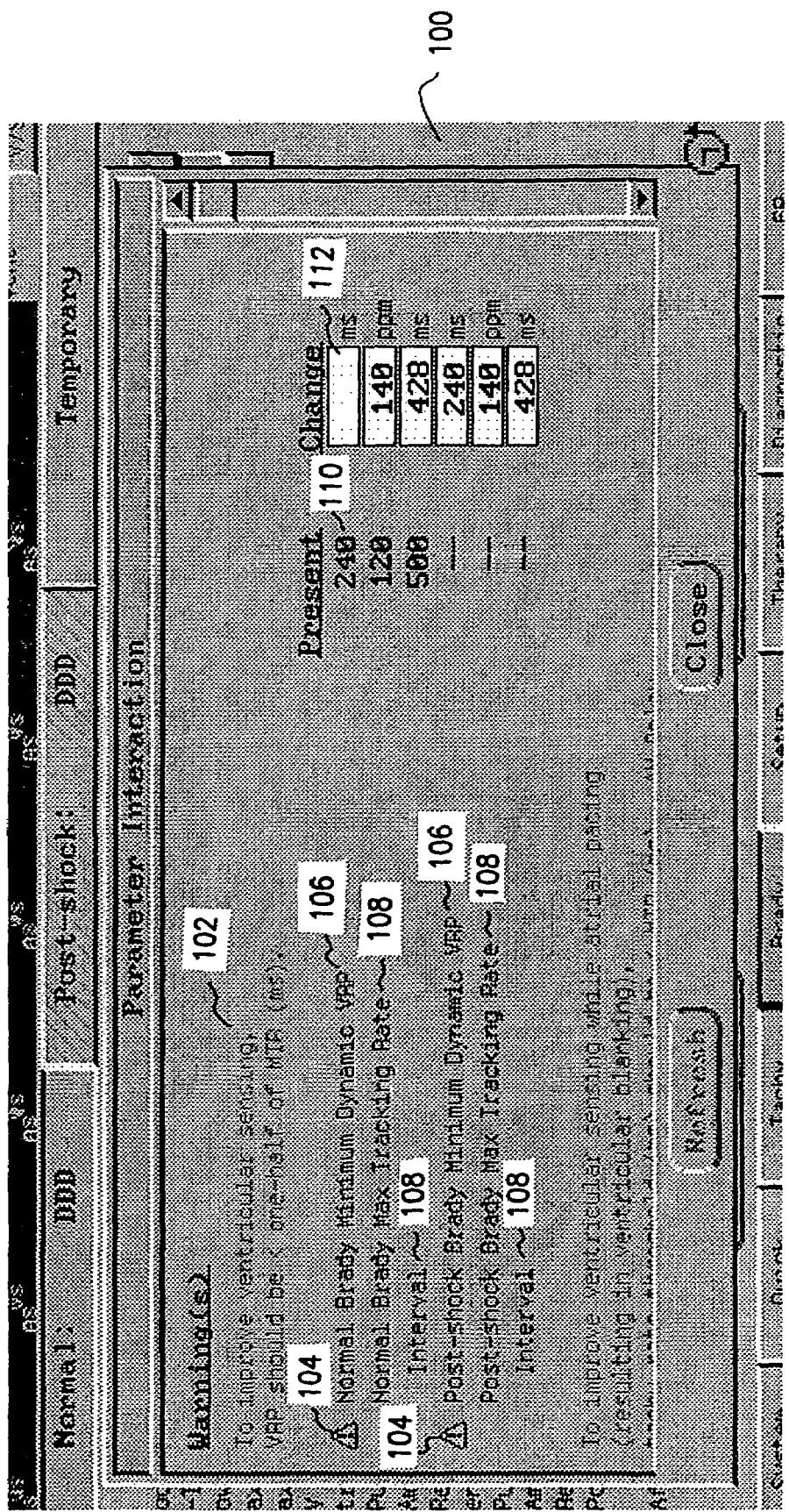
FIGS. 8–10 are examples of parameter interaction warning displays.

One visual display which can be used to provide such feedback is shown in FIG. 8. The example in FIG. 8 is based on the defibrillator example of FIG. 3 but could be extended to other medical devices.

In display 100 of FIG. 8, feedback is provided to the user in the form of a warning 102, an icon 104 and one or more parameters 106. In addition, display 100 may include parameters 108. Warning 102 gives the reason why the suggested programming settings are not allowed. Icon 104 designated the status of the suggested programming change (in this scenario, icon 104 is a yellow warning icon as described above). Parameters 106 are the parameters in question while parameters 108 are the additional parameters which may need to be adjusted. Finally, there is a present value 110 and a change box 112 for each parameter 106 and 108.

Figure 9:
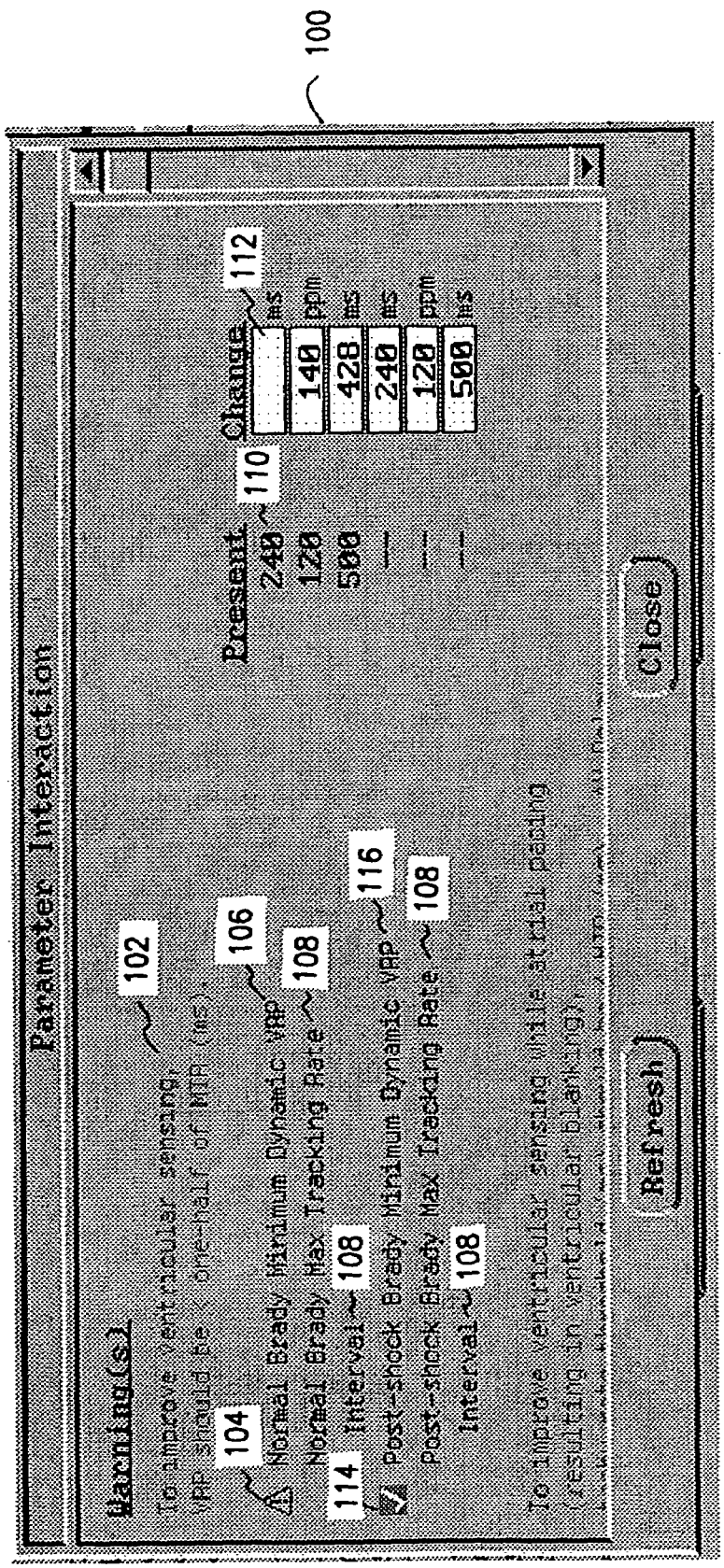

In one embodiment, changes to parameters 106 and 108 are displayed immediately, with a visual confirmation of the success or failure of the change in programming. An example of a successful change in programming is shown in FIG. 9. In FIG. 9, a change to the Post-shock Brady Max Tracking Rate (from 140 ppm in FIG. 8 to 120 ppm in FIG. 9) results in an acceptable Post-shock Brady Minimum Dynamic VRP parameter 116. As a result, a positive icon 114 is displayed next to parameter 116. (In this scenario, icon 114 is a green check icon as described above. Other symbols of correctness could also be used.) Note that the possible problem with Normal Brady Minimum Dynamic VRP parameter 106 remains uncorrected at this time.

Figure 10:
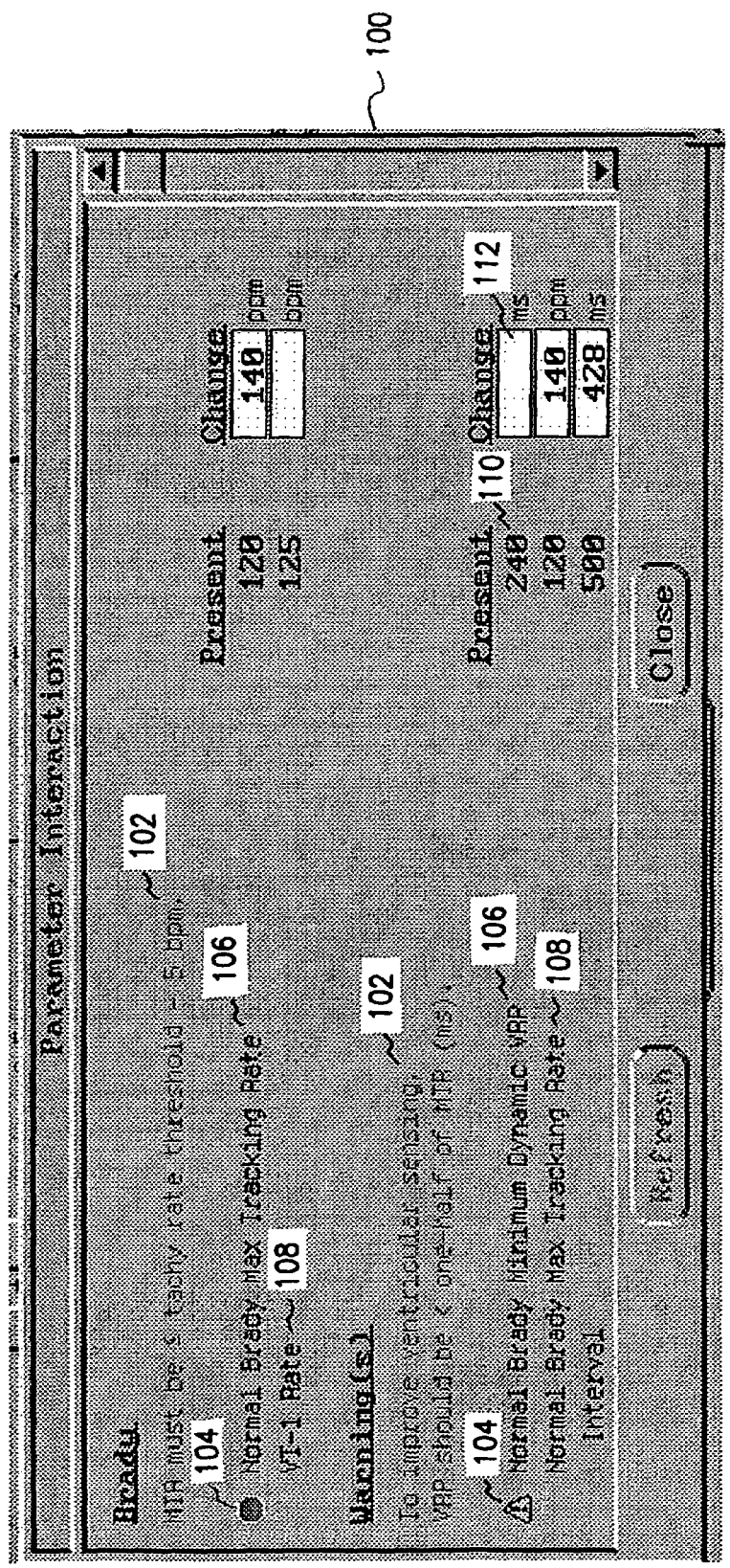

Another example of parameter interaction is shown in FIG. 10. In FIG. 10, feedback is provided to the user in the form of a warning 102, an icon 104 and one or more parameters 106. In addition, display 100 may include parameters 108. As in FIG. 8, warning 102 gives the reason why the suggested programming settings are not allowed. Icon 104 designated the status of the suggested programming change (in this scenario, the first icon 104 is a red stop sign icon while the second icon 104 is a yellow warning icon). Parameters 106 are the parameters in question while parameters 108 are the additional parameters which may need to be adjusted. Finally, there is a present value 110 and a change box 112 for each parameter 106 and 108.

In one embodiment, when a new parameter is entered in the Change column of display 100, it is immediately checked for interactions with other parameters. This may be done, for example, by a review of the set of rules discussed above. If the new value violates interactive limits within the application, a parameter interaction stop sign is displayed as discussed above. In one such embodiment, this icon can be selected to access a parameter interaction screen such as is displayed in FIGS. 8–10. Once the parameter interaction screen is accessed, the user can make changes directly from within the window.

Similarly, if the new value creates a situation where the value is not forbidden but more information should be presented to the clinician, the warning sign icon is displayed. In one such embodiment, this icon can be selected to access a parameter interaction screen such as is displayed in FIGS. 8–10. Changes to the affected parameter or parameters need not be made in order to proceed. Physician discretion is, however, advised depending on the type of patient or on other circumstances relating to the device.

One should be careful when writing the rules which detect and display parameter interactions. Each warning should include a description of the present clinical situation, the present equation at issue and suggestions for resolving the issue. The rules and the warnings must be coordinated to present meaningful warnings for all combinations of parameter interactions.

In contrast to previous devices, this method of handling parameter interaction provides a more intuitive approach coupled with the capability to provide the user immediate feedback on the choices they have made. This saves time for the user. In addition, by allowing the user to make all necessary changes from one screen, rather than having to navigate through multiple screens, ease of use is improved.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. Therefore, it is intended that this invention be limited only by the claims and the equivalents thereof.

What is claimed is:

1. A system, comprising:
    means for determining whether entered parameters for a programmable medical device acceptably interact with each other according to a set of rules;
    means for providing a visual status indicator based on the entered parameters and the set of rules; and
    means for providing a feedback message for entered parameters that do not acceptably interact with each other, wherein the feedback message includes a suggestion for how to change the entered parameters to resolve unacceptable parameter interaction.

2. The system of claim 1, wherein the means for providing a visual status indicator based on entered parameters and the set of rules includes means for providing a visual indicator that the parameters acceptably interact.

3. The system of claim 1, wherein the means for providing a visual indicator that the parameters acceptably interact with each other includes means for providing a green check icon next to each acceptable parameter.

4. The system of claim 1, wherein the means for providing a visual status indicator based on entered parameters and the set of rules includes means for providing a visual indicator that the parameters do not acceptably interact with each other.

5. The system of claim 4, wherein the means for providing a visual indicator that the parameters do not acceptably interact with each other includes means for providing a red stop sign icon next to each parameter that does not acceptably interact with each other.

6. The system of claim 4, wherein the means for providing a feedback message for entered parameters that do not acceptably interact with each other includes means for displaying a reason why the parameters do not acceptably interact with each other.

7. The system of claim 4, where the means for providing a feedback message for entered parameters that do not acceptably interact with each other includes means for displaying a suggestion for changing the parameters that do not acceptably interact with each other.

8. The system of claim 4, further comprising:
    means for determining that at least one unacceptable parameter has been changed to at least one acceptable parameter; and means for changing the visual indicator that the parameters do not acceptably interact with each other to a visual indicator that the parameters acceptably interact with each other.

9. The system of claim 1, wherein the means for providing a visual status indicator based on entered parameters and the set of rules includes means for providing a visual indicator that provides a warning to use discretion based on parameter interaction.

10. The system of claim 9, wherein the means for providing a visual indicator that provides a warning to use discretion with respect to the parameters includes means for providing a yellow warning icon next to each parameter for which discretion should be used.

11. The system of claim 9, wherein the means for providing a visual status indicator based on entered parameters and the set of rules includes:
means for providing a visual indicator for one or more acceptable parameters;
means for providing a visual indicator for one or more allowable parameters indicating a warning to use discretion with respect to the allowable parameters; and
means for providing a visual indicator for one or more unacceptable parameters.

12. The system of claim 11, wherein:
the means for providing a visual indicator for one or more acceptable parameters includes means for providing a green check icon next to each acceptable parameter;
the means for providing a visual indicator for one or more allowable parameters indicating a warning to use discretion with respect to the allowable parameters includes means for providing a yellow warning icon next to each allowable parameter for which discretion should be used; and
the means for providing a visual indicator for one or more unacceptable parameters includes means for providing a red stop sign icon next to the each unacceptable parameter.

13. The system of claim 11, wherein the means for providing a feedback message for entered parameters that do not acceptably interact includes means for displaying a reason why the parameters do not acceptably interact.

14. The system of claim 11, wherein the means for providing a feedback message for entered parameters that do not acceptably interact includes means for displaying a suggestion for changing the parameters that do not acceptably interact.

15. The system of claim 11, further comprising:
means for determining that at least one unacceptable parameter has been changed to at least one acceptable parameter; and
means for changing the visual indicator that the parameters do not acceptably interact to a visual indicator that the parameters acceptably interact.

16. A system, comprising:
means for determining whether entered parameters for a programmable medical device acceptably interact with each other according to a set of rules; and
means for providing a visual status indicator based on entered parameters and the set of rules, including:
means for providing a visual indicator of a first color for one or more acceptable parameters;
means for providing a visual indicator of a second color for one or more allowable parameters indicating a warning to use discretion with respect to interaction of the allowable parameters to other entered parameters; and
means for providing a visual indicator of a third color for one or more unacceptable parameters.

17. The system of claim 16, wherein:
the means for providing a visual indicator of a first color for one or more acceptable parameters includes means for providing a green check icon next to each acceptable parameter;
the means for providing a visual indicator of a second color for one or more allowable parameters indicating a warning to use discretion includes means for providing a yellow warning icon next to each allowable parameter for which discretion should be used; and
the means for providing a visual indicator of a third color for one or more unacceptable parameters includes means for providing a red stop sign icon next to the each unacceptable parameter.

18. The system of claim 16, further comprising:
means for determining that at least one unacceptable parameter has been changed to at least one acceptable parameter; and
means for changing the visual indicator that the parameters do not acceptably interact with each other to a visual indicator that the parameters acceptably interact with each other.

19. The system of claim 16, further comprising means for providing a feedback message for entered parameters that do not acceptably interact with each other.

20. The system of claim 19, wherein the feedback message is a text message.

21. The system of claim 19, wherein the means for providing a feedback message for entered parameters that do not acceptably interact with each other includes means for displaying a reason why the parameters do not acceptably interact with each other.

22. The system of claim 19, wherein the means for providing a feedback message for entered parameters that do not acceptably interact with each other includes means for displaying a suggestion for changing the parameters that do not acceptably interact with each other.

23. A system, comprising:
means for identifying parameter interactions between feature parameters;
means for defining a plurality of messages, wherein the plurality of messages includes a first type of message, a second type of message and a third type of message, wherein the first type of message indicates correctness, wherein the second type of message warns of a parameter interaction and wherein the third type of message warns of impermissible parameter settings;
means for associating each of the parameter interactions with one of the message types;
means for accepting a parameter value;
means for examining the parameter value to determine if it causes a parameter interaction;
means for displaying a message of the first message type for one or more acceptable parameters;
means for displaying a message of the second message type indicating a warning to use discretion with respect to interaction of the feature parameters; and
means for displaying a message of the third message type for one or more unacceptable parameters.

24. The system of claim 23, wherein the plurality of messages includes icons indicating a level of correctness.

25. The system of claim 23, wherein the plurality of messages includes a suggestion for how to change the parameter value to resolve unacceptable parameter interaction.

* * * * *